(12) United States Patent
Howlett et al.

(10) Patent No.: US 8,480,682 B2
(45) Date of Patent: Jul. 9, 2013

(54) DEVICE FOR LIMITING THE DRILLING DEPTH OF A DRILL

(75) Inventors: Charles Howlett, Laguna Beach, CA (US); Kim Nguyen, San Diego, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 985 days.

(21) Appl. No.: 12/550,200

(22) Filed: Aug. 28, 2009

(65) Prior Publication Data

US 2011/0054483 A1 Mar. 3, 2011

(51) Int. Cl.
*A61B 17/58* (2006.01)

(52) U.S. Cl.
USPC .......................................................... 606/96

(58) Field of Classification Search
USPC ............................................. 606/96; 408/202
See application file for complete search history.

(56) References Cited

U.S. PATENT DOCUMENTS

| 74,466 | A | * | 2/1868 | Whiting | 408/202 |
| 2,231,864 | A | * | 2/1941 | Abel | 408/202 |
| 4,521,145 | A | * | 6/1985 | Bieler | 409/218 |
| 7,261,499 | B2 | * | 8/2007 | Mathis et al. | 408/202 |
| 2005/0147478 | A1 | * | 7/2005 | Greenberg | 408/241 S |
| 2009/0318927 | A1 | * | 12/2009 | Martin et al. | 606/96 |
| 2010/0172706 | A1 | * | 7/2010 | Wirth et al. | 408/224 |
| 2010/0215450 | A1 | * | 8/2010 | Santamarina et al. | 408/113 |

* cited by examiner

*Primary Examiner* — Kevin T Truong
*Assistant Examiner* — Michael Araj
(74) *Attorney, Agent, or Firm* — Schwegman, Lundberg & Woessner P.A.

(57) ABSTRACT

A stop is used for limiting the drill depth of an osteotomy drill bit within a bore in bone. This stop may have a generally tubular body for being releasably mounted on the drill bit and have a cam slot disposed at the body and used for defining a plurality of axial positions. The cam slot is configured for releasably securing a cam follower associated with a drill assembly that extends radially relative to a longitudinal axis of the drill bit assembly to axially secure the stop to the drill bit assembly. Additionally, the stop includes an apical end section that is configured to engage bone adjacent to the bore and limit the apical motion of the drill bit.

20 Claims, 4 Drawing Sheets

DEVICE FOR LIMITING THE DRILLING DEPTH OF A DRILL

FIELD OF THE INVENTION

The present invention relates to a device for attachment to an osteotomy drill, and in particular, a drill device for controlling bore depth in a bone.

BACKGROUND OF THE INVENTION

Dental drills are generally used during a surgical procedure to create a bore in a mandible or maxilla suitable for receiving a dental implant or other dental device. Certain surgical procedures require drilling multiple bores having a variety of depths for receiving different sized dental implants or devices. To create these multiple sized bores, markings may be made on the drill bit by the practitioner to indicate the depth to stop forward motion of the bit. This, however, is often inaccurate. Otherwise a practitioner often uses multiple drill bits of varying lengths so that each drill bit provides a unique drilling depth. In one case, the bore is drilled until a part of the drill reaches the bone around the opening to the bore. This requires the practitioner to interchange multiple different drill bits with the drill handpiece during the surgical procedure. Such a process can be both difficult and time consuming for the practitioner and may increase the overall time necessary to complete the surgical procedure.

Optionally a separate stop is connected to the drill bit to stop the advancement of the drill bit. For the separate stop, a sleeve is mounted on the drill bit to create the desired bit length. Either sleeves of different lengths are provided where each length corresponds to a desired drill depth or a single sleeve is cut to a desired length before mounting it on the drill bit.

In yet another conventional example, an adjustable collar is set to a specific axial location along the drill bit, which corresponds to a particular drill depth. The drill bit may be advanced into bone until the adjustable collar abuts against surrounding bone at the entrance to the bore, thereby preventing further forward axial movement of the drill bit. The practitioner may drill a bore having a different depth by reconfiguring the adjustable collar to a different axial location along the drill bit corresponding to the different bore depth. In this example, the practitioner adjusts the axial location of the adjustable collar relative to the drill bit by using a tool to unfasten a screw that extends through the collar to the drill bit. Once the screw is unfastened, the adjustable collar can be moved to a new location, and the screw then re-tightened to the drill bit with the tool. This process is time consuming and inconvenient. Such screws are susceptible to damage, contamination, and/or being dropped while changing the position of the collar. Thus, a stopping mechanism is desired that is quickly and conveniently adjusted to different positions on a drill bit.

DETAILED DESCRIPTION OF THE PREFERRED EMBODIMENT

Figure 1:
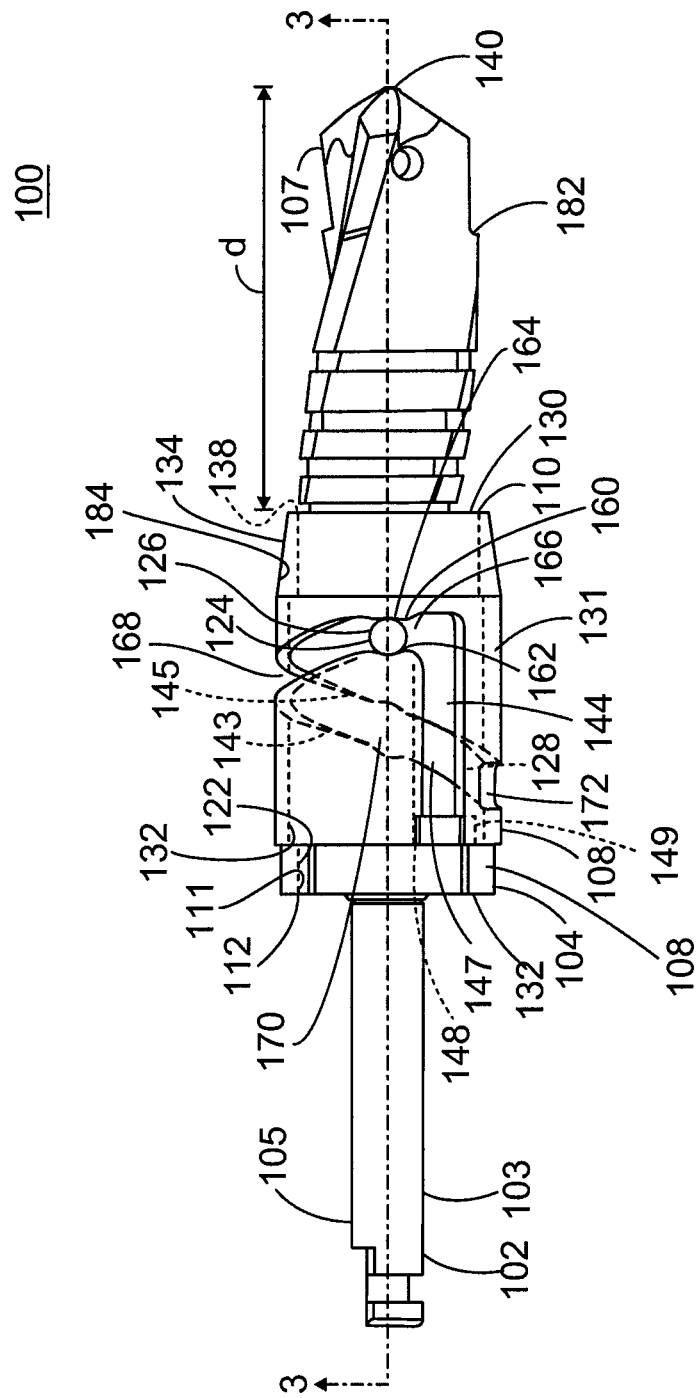
FIG. 1 is a side elevational view of a drill bit assembly embodying features of the present invention.
Figure 2:
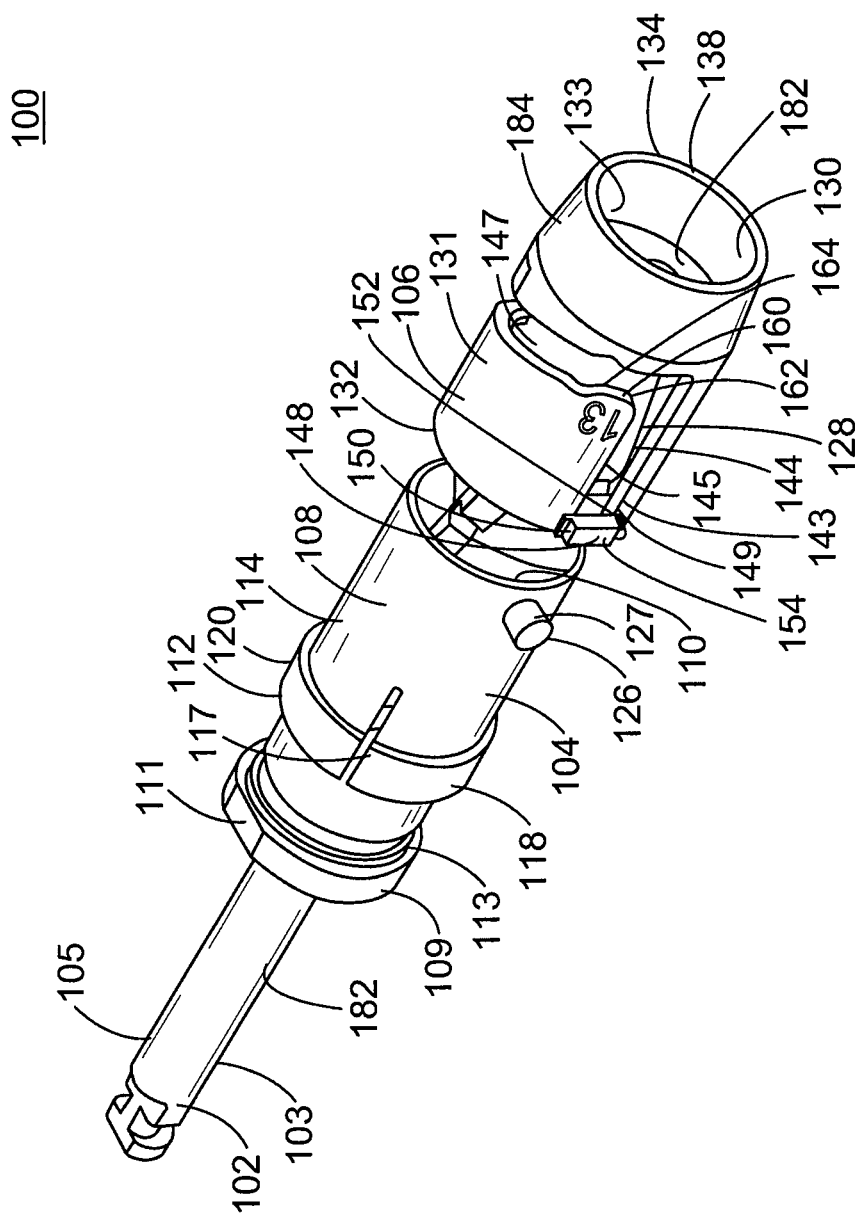
FIG. 2 is an exploded perspective view of the drill bit assembly of FIG. 1 embodying features of the present invention.
Figure 3:
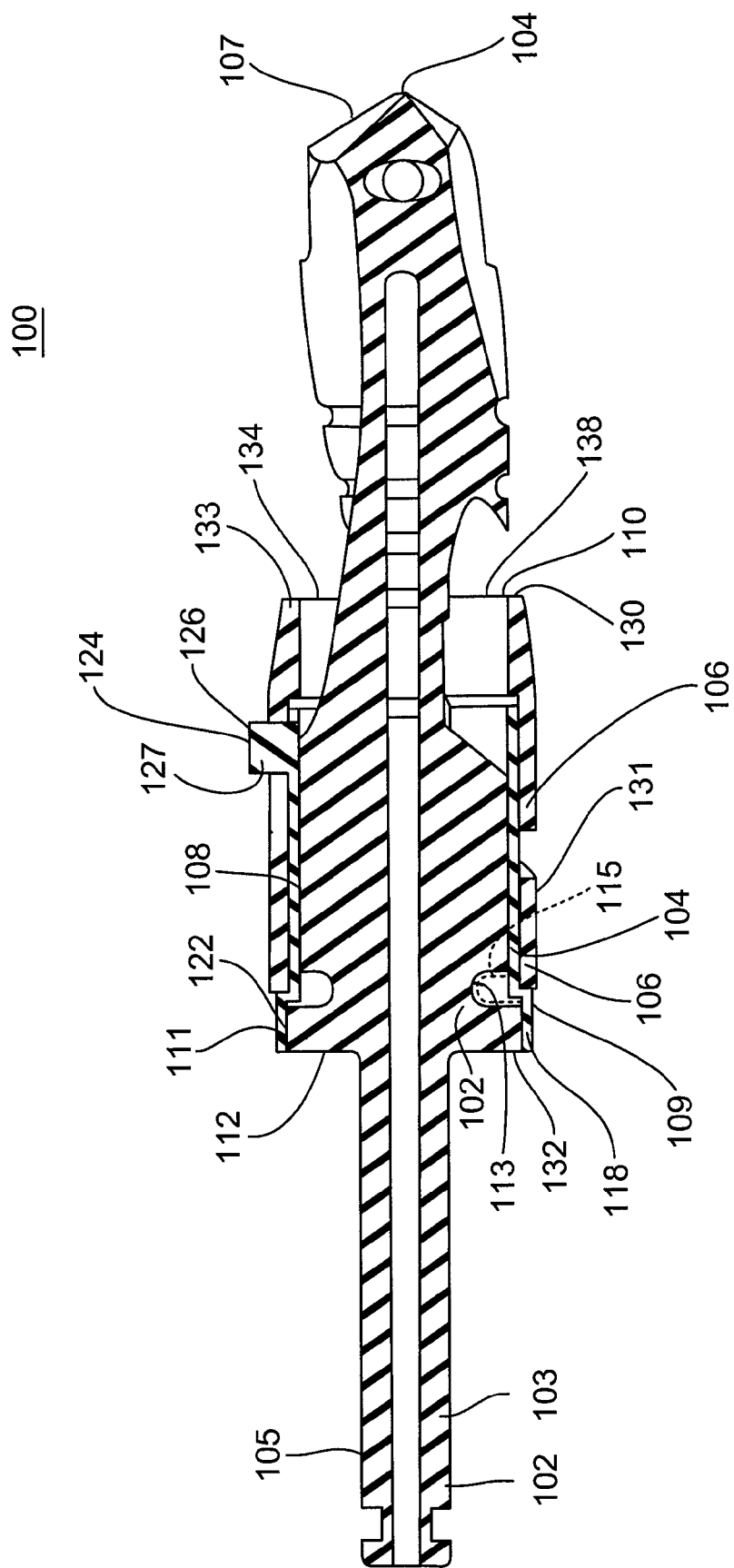
FIG. 3 is a side cross-sectional view of the drill bit assembly of FIG. 1 embodying features of the present invention.

Referring to FIGS. 1-3, a drill bit assembly 100 has a drill bit 102, a sleeve 104, and an adjustable stop 106 configured to limit the drill depth of an osteotomy drill within a bore in bone. This drill bit assembly 100 provides a practitioner with careful and precise control over the size of a bore and the depth of the bore being drilled. In particular, this assembly provides added safety against a practitioner drilling a bore too deep and breaching into the sinus floor or into the mandibular canal which could cause considerable harm to a patient. Moreover, this assembly provides a sanitary and easy way for the practitioner to disassemble and clean the drill bit assembly 100 between surgical procedures.

The drill bit 102 has an elongate body 103 including a coronal stem portion 105 for attachment to a drill handpiece and an apical cutting portion 107. The cutting portion 107 of the drill bit includes a tip portion 140 configured to engage a bone in the patient's mouth and form a bore capable of receiving a dental implant or other dental device. The cutting portion 107 also has a generally circular flange portion 109 with at least one flat 111 to secure the sleeve 104 on the drill bit as explained below. The drill bit 102 is made of metal such as stainless steel.

The sleeve 104 attaches the adjustable stop 106 to the drill bit assembly 100. In one example, the sleeve 104 may be made from a stainless steel or material with similar strength. The sleeve 104 has a generally tubular body 108 with a hollow interior 180, an apical opening 110, and a coronal opening 112. Moreover, the sleeve 104 has an outer surface 114 and an inner surface 116 that is configured to fit over and engage an outer surface 182 of the drill bit 102. In one example, the sleeve 104 may also include a coronal lip 118 disposed along a coronal section 120 of the sleeve. To rotationally secure the sleeve 104 on the drill bit, the coronal lip 118 has an interior flat 122 that engages the flat 111 of the drill bit 102.

The sleeve may have one or more axial grooves 117 to permit the coronal lip 118 to flex, thereby applying radial pressure to the flange 109, and/or the flat 111 when engaged to provide a tight or friction fit.

As another option, to axially secure the sleeve 104 to the drill bit 102, the sleeve 104 may have one or more interiorly extending and circumferentially spaced protrusions 115 that are snap-fit into groove 113 on drill bit 102. For this option, the protrusion 115 may be a complete ring, or the coronal lip 118 of the sleeve 104 may snap-fit on the flange portion 104 of the drill bit 102 instead of the groove connection. In either case, the sleeve 104 may have one or more grooves 117 to permit the coronal lip 118 to flex to snap-fit the sleeve 104 onto the drill bit 102.

In alternative, or additionally to, the flat 111, an axial groove may be provided in the flange 109 and a mating anti-rotation projection provided in the interior of the coronal lip 118 to engage the groove.

The sleeve 104 and stop 106 are releasably attached to each other by a cam follower 124. Thus, the stop 106 has a cam slot that receives a cam follower 124 on the sleeve. The cam slot defines a plurality of predetermined axial positions along its length to define different axial positions for the adjustable stop 106 relative to the sleeve 104 and drill bit 102. In the illustrated example, the sleeve 104 has a cam follower 126 that extends radially outward from the outer surface 114 to engage a corresponding cam slot 128 extending on the adjustable stop 106. In this example, the cam follower 126 has a generally cylindrical outer surface 127.

In the illustrated example, the cam follower 126 extends completely through the cam slot 128. It will be understood, however, that the cam slot may be closed to form an elongate channel with a bottom, and the cam follower 126 merely extends into the slot rather than completely through.

The adjustable stop 106 has a generally tubular body 184 made of a polymer or other resilient material, an apical opening 130, a coronal opening 132, an outer surface 131, and an inner surface 133. In one form, the stop 106 has an apical end section 134 with a rim 138 configured to make contact with bone surrounding the bore, thereby limiting apical motion of the drill bit.

The cam slot 128 is formed by two opposite elongate edges 143 and 145 that are spaced a distance from one another so as to allow the cam follower 126 to slide within the cam slot 128. The cam slot 128 also defines a plurality of axial positions 166, 168, 170, and 172. In one form, each position has at least one protrusion, but here two opposite protrusions 160 and 162, that extend inward from outer edges 143 and/or 145 and are shaped to secure the cam follower 126 at the axial position. The protrusions are shaped to receive the cam follower 126 in a snap-fit that is sufficient to secure the stop 106 both rotationally and axially relative to the sleeve 104 and, in turn, drill bit 102, while the drill bit undergoes relatively high speed rotation, unless an external force acts on the stop, such as by hand. In one example, the opposite protrusions 160 and 162 form curved, opposite, concave surfaces 164 that correspond to, and engage, the generally cylindrical cam follower 126. For the snap-fit, the opposite protrusions 160 and 162 are spaced a distance apart from one another that is narrower than the width of the cam follower 126. Since the stop 106 is made of a resilient material, the two opposing protrusions 160 and 162 shift away from each other as the cam follower 126 is pressed against the protrusions and onto the curved surfaces 164. So configured, the protrusions move back to their natural distance apart, thereby securing the cam follower 126 in the predetermined position 166, 168, 170, and 172. Additionally, a slot may be provided proximate the protrusions 160 and 162 to provide additional flexure to the material for engagement. In one example, the slot may be located on the outer surface 131, the inner surface 133, or may extend through both the outer surface 131 and the inner surface 133.

The cam slot 128 may include an axial section 144 and a spiral section 147. In this example, the axial section 144 extends from a coronal end 149 of the stop, where the slot 128 opens to receive the cam follower 126 of the sleeve. The spiral section 147 extends circumferentially from the axial section 144 while extending generally axially about the stop 106. In one form, the positions 166, 168, 170, and 172 are defined on the spiral section 147. In the illustrated form, the positions 166, 168, 170, and 172 are circumferentially spaced at 90 degree intervals around the stop 106. In this example, the four positions 166, 168, 170 and 172 correspond to four distinct axial positions for the adjustable stop 106 relative to the drill bit 102. Specifically, a distance 'd' is defined from the rim 138 of the adjustable stop 106 to the apical-most tip of the cutting portion 107 of the drill bit 102. As the adjustable stop 106 is rotated such that the cam follower 126 is disposed at an axial position 166, 168, 170, or 172, the distance 'd' increases or decreases depending on the position.

In one example, the axial positions 166, 168, 170, and 172 have respective associated distances 'd' of 13 mm, 11.5 mm, 10 mm, and 8 mm. It will be understood that the number of positions and distances 'd' associated with the different positions may vary.

The stop 106 may also include a strengthening bridge 148 that spans a portion of the cam slot 128. The strengthening bridge 148 may include opposite end sections or columns 150 and 152 that extend radially outward from the outer surface 131 of the stop 106. A beam 154 spans columns 150 and 152. The shape of the strengthening bridge 148, however, may vary. In this example, the strengthening bridge 148 may span the axial section 144 of the cam slot 128, and may be spaced from the slot 128 so as to provide clearance for the cam follower 126 to slide past the bridge 148 and into the cam slot 128.

In operation, once the adjustable stop 106 is adjusted to a particular axial position 166, 168, 170, or 172, the drilling procedure may commence. As the tip 140 of the drill bit 102 engages the bone, a bore will form. The drill bit 102 is advanced in an apical direction during the drilling procedure until the rim 138 of the stop 106 contacts the bone surrounding the bore. When this occurs, the practitioner feels the resistance of the rim 138 contacting the bone, and the advancement of the drill into the bore is stopped.

Figure 4:
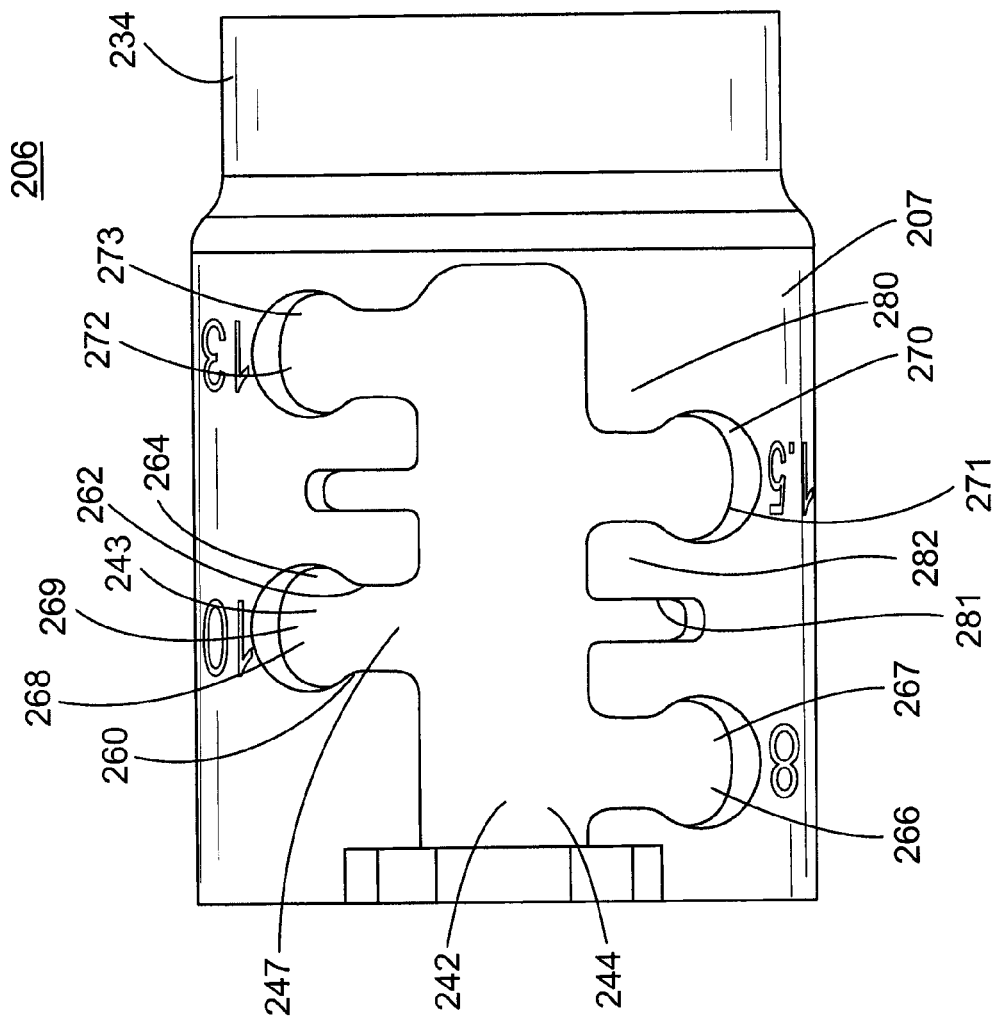
FIG. 4 is a perspective view of an alternative adjustable stop having a cam slot embodying features of the present invention.

In an alternative example and referring to FIG. 4, the drill bit assembly 100 disclosed in FIGS. 1-3, includes an adjustable stop 206, instead of stop 106. Similar to the disclosure above, the adjustable stop 206 may be a generally tubular body 207 that may be made of a polymer or other resilient material. The stop 206 has an apical end section 234 configured to engage bone.

The stop 206 also has a cam slot 242 to receive cam follower 124. The cam slot 242 has an axial section 244 and at least one transverse branch section 247. Here, four branch sections 266, 268, 270, and 272 extend generally perpendicular to the axial section 244 although other directions are contemplated such as diagonal. Each branch section 266, 268, 270, and 272 defines an axial position, and includes a corresponding reception or holding area 267, 269, 271, and 273 that opens to a closed section 264. In this example, the branch sections 266, 268, 270, and 272 have respective associated distances 'd' of 8 mm, 10 mm, 11.5 mm, 13 mm. Each reception area 267, 269, 271, and 273 includes opposite edges 260 and 262 that secure the cam follower 126 in the closed section 264. In one form, the opposite edges 260 and 262 may extend generally parallel to one another and perpendicular to the axial section 244. In this example, the opposite edges 260 and 262 are part of two resilient pieces or projections 280 and 282 that are spaced a distance apart from one another but at a distance narrower than the width of the cam follower 126. A groove 281 is provided on projection 282 between adjacent branches to increase resiliency of the edges 260 and 262. This configuration permits the cam follower 126 to be pressed past the two resilient opposing edges 260 and 262 and snap-fit into the closed section 264.

In another example, the sleeve portion is not present. Instead, the drill bit includes a radially extending cam follower to engage the cam slot of the adjustable stop thereby releasably securing the adjustable stop to the drill bit.

In another example, the stop may have the cam follower to engage a cam slot disposed on the sleeve.

While the drill bit assembly is mainly described herein for use with a dental surgical procedure, it will be understood that the drill bit assembly may be used with other bone implant surgeries used on other areas of a human body or an animal.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. Further, this application is intended to cover such departures from the present disclosure as come within known or customary practice in the art to which this invention pertains and which fall within the limits of the appended claims.

What is claimed is:

1. A stop for limiting the drill depth of an osteotomy drill bit within a bore in bone, the drill bit defining a longitudinal axis, the stop comprising:
    a generally tubular body for being releasably mounted on the drill bit;
    a cam slot disposed at the body and defining a plurality of axial positions configured for releasably securing a cam follower extending radially relative to the longitudinal axis to axially secure the stop to the drill bit, wherein the cam slot is formed by two opposing elongate edges, the two edges forming at least one protrusion to form a snap-fit with the cam follower to releasably secure the cam follower at one of the plurality of axial positions; and
    an apical end section configured to engage bone adjacent to the bore and limit the apical motion of the drill bit.

2. The stop for of claim 1 wherein the cam slot has an axial section and a spiral section extending circumferentially from the axial section, the spiral section defining the plurality of axial positions.

3. The stop of claim 1 wherein the cam slot includes an axial section and at least two transverse branch sections extending generally perpendicular to the axial section to define the plurality of axial positions.

4. The stop of claim 1 wherein the cam slot comprises pairs of opposing transverse branch sections.

5. The stop of claim 1 wherein each one of the plurality of axial positions are circumferentially spaced at 90 degree intervals.

6. The stop of claim 1 wherein the stop is made of a resilient material.

7. The stop of claim 1 wherein the cam slot includes an axially extending section configured to mount the stop to the cam follower.

8. The stop for of claim 1 further comprising a strengthening bridge spanning the cam slot while being configured to provide clearance for the cam follower to slide past the bridge and within the slot.

9. The stop of claim 1 wherein the stop is mounted on a sleeve mounted on the drill bit, the cam follower extending radially outward from the sleeve.

10. A drill stop assembly for limiting the drill depth of an osteotomy drill bit in a bore in bone, the assembly comprising:
    a sleeve for being axially secured to the drill bit and having an outer surface;
    a stop being configured to be releasably secured on the outer surface of the sleeve at one of a plurality of predetermined axial positions, the stop having an apical end section to engage the bone adjacent the bore to limit the apical motion of the drill bit; and
    a cam connection configured for selectively disposing the stop at a selected one of the plurality of predetermined axial positions wherein one of the sleeve and stop comprises a radially extending cam follower, and the other of the sleeve or stop forms a cam slot for receiving and guiding the cam follower and for defining the plurality of predetermined axial positions, wherein the cam slot is formed by two opposing elongate edges, the two edges forming at least one protrusion to form a snap-fit with the cam follower to releasably secure the cam follower at one of the plurality of axial positions.

11. The drill stop assembly of claim 10 wherein the sleeve comprises an anti-rotational surface for rotationally securing the sleeve to the drill bit and one of a protrusion and recess for axially securing the sleeve to the drill bit.

12. The drill stop assembly of claim 10 wherein the two edges have opposing protrusions for holding the cam follower.

13. The drill stop assembly of claim 10 wherein the cam follower has a generally cylindrical outer surface and the at least one protrusion forms a curved concave surface for receiving the outer surface.

14. The drill stop assembly of claim 13 wherein the two edges each have a curved concave surface opposing each other.

15. The drill stop assembly of claim 10 wherein the at least one protrusion comprises two resilient opposing protrusions spaced a distance apart narrower than a width of the cam follower, the two resilient opposing protrusions opening to a closed section of the cam slot so that pressing the cam follower past the two opposing protrusions secures the cam follower at the closed section.

16. A stop for limiting the drill depth of an osteotomy drill bit within a bore in bone, the drill bit defining a longitudinal axis, the stop comprising:
    a generally tubular body for being releasably mounted on the drill bit;
    a cam slot disposed at the body and defining a plurality of axial positions configured for releasably securing a cam follower extending radially relative to the longitudinal axis to axially secure the stop to the drill bit;
    a strengthening bridge spanning the cam slot while being configured to provide clearance for the cam follower to slide past the bridge and within the slot; and
    an apical end section configured to engage bone adjacent to the bore and limit the apical motion of the drill bit.

17. The stop for of claim 16 wherein the cam slot has an axial section and a spiral section extending circumferentially from the axial section, the spiral section defining the plurality of axial positions.

18. The stop of claim 16 wherein the cam slot includes an axial section and at least two transverse branch sections extending generally perpendicular to the axial section to define the plurality of axial positions.

19. The stop of claim 16 wherein the cam slot comprises pairs of opposing transverse branch sections.

20. The stop of claim 16 wherein each one of the plurality of axial positions are circumferentially spaced at 90 degree intervals.

* * * * *